United States Patent
Tapolsky et al.

(10) Patent No.: US 7,579,019 B2
(45) Date of Patent: Aug. 25, 2009

(54) PHARMACEUTICAL CARRIER DEVICE SUITABLE FOR DELIVERY OF PHARMACEUTICAL COMPOUNDS TO MUCOSAL SURFACES

(75) Inventors: Gilles H. Tapolsky, The Woodlands, TX (US); David W. Osborne, The Woodlands, TX (US)

(73) Assignee: Arius Two, Inc., Raleigh, NC (US)

( * ) Notice: Subject to any disclaimer, the term of this patent is extended or adjusted under 35 U.S.C. 154(b) by 835 days.

(21) Appl. No.: 11/069,089

(22) Filed: Mar. 1, 2005

(65) Prior Publication Data
US 2005/0147658 A1    Jul. 7, 2005

Related U.S. Application Data

(60) Continuation of application No. 09/684,682, filed on Oct. 4, 2000, now abandoned, which is a division of application No. 09/069,703, filed on Apr. 29, 1998, now abandoned, which is a continuation-in-part of application No. PCT/US97/18605, filed on Oct. 16, 1997.

(51) Int. Cl.
*A61F 13/00* (2006.01)
*A61K 9/14* (2006.01)
(52) U.S. Cl. .......................... 424/435; 424/486
(58) Field of Classification Search .............. 424/435, 424/486
See application file for complete search history.

(56) References Cited

U.S. PATENT DOCUMENTS

| | | | |
|---|---|---|---|
| 3,640,741 A | 2/1972 | Estes | |
| 3,996,934 A | 12/1976 | Zaffaroni | |
| 4,226,848 A | 10/1980 | Nagai et al. | |
| 4,250,163 A | 2/1981 | Nagai et al. | |
| 4,285,934 A | 8/1981 | Tinnell | |
| 4,286,592 A | 9/1981 | Chandrasekaram | |
| 4,292,299 A | 9/1981 | Suzuki | |
| 4,381,296 A | 4/1983 | Tinnell | |
| 4,517,173 A | 5/1985 | Kizawa et al. | |
| 4,518,721 A | 5/1985 | Dhabhar et al. | |
| 4,552,751 A | 11/1985 | Inaba et al. | |
| 4,572,832 A | 2/1986 | Kigasawa et al. | |
| 4,594,240 A | 6/1986 | Kawata et al. | |
| 4,668,232 A | 5/1987 | Cordes | |
| 4,713,243 A | 12/1987 | Schiraldi et al. | |
| 4,713,246 A | 12/1987 | Begum et al. | |

(Continued)

FOREIGN PATENT DOCUMENTS

CA    2169729    4/2001

(Continued)

OTHER PUBLICATIONS

The Merck Manual, http://www.merck.com/mmhe/sec06/ch078/ch078a.html?qt=pain&alt=sh, obtained online on Aprkl 9 2009.*

(Continued)

*Primary Examiner*—Johann R Richter
*Assistant Examiner*—Abigail Fisher
(74) *Attorney, Agent, or Firm*—McCarter & English LLP (57) ABSTRACT

The present invention relates to a pharmaceutical delivery device for application of a pharmaceutical to mucosal surfaces. The device comprises an adhesive layer and a non-adhesive backing layer, and the pharmaceutical may be provided in either or both layers. Upon application, the device adheres to the mucosal surface, providing localized drug delivery and protection to the treatment site. The kinetics of erodability are easily adjusted by varying the number of layers and/or the components.

7 Claims, 1 Drawing Sheet

U.S. PATENT DOCUMENTS

| | | | |
|---|---|---|---|
| 4,715,369 A | 12/1987 | Suzuki et al. | |
| 4,720,387 A | 1/1988 | Sakamoto et al. | |
| 4,740,365 A | 4/1988 | Yukimatsu et al. | |
| 4,755,386 A | 7/1988 | Hsiao et al. | |
| 4,764,378 A | 8/1988 | Keith et al. | |
| 4,765,983 A | 8/1988 | Takayanagi et al. | |
| 4,784,858 A | 11/1988 | Ventouras | |
| 4,857,336 A | 8/1989 | Khanna et al. | |
| 4,867,970 A | 9/1989 | Newsham et al. | |
| 4,876,092 A | 10/1989 | Mizobuchi et al. | |
| 4,889,720 A | 12/1989 | Konishi | |
| 4,894,232 A | 1/1990 | Reul et al. | |
| 4,900,552 A | 2/1990 | Sanvordeker et al. | |
| 4,900,554 A | 2/1990 | Yanagibashi et al. | |
| 4,906,463 A | 3/1990 | Cleary et al. | |
| 4,915,948 A | 4/1990 | Gallopo et al. | |
| 4,990,339 A | 2/1991 | Scholl et al. | |
| 5,047,244 A | 9/1991 | Sanvordeker et al. | |
| 5,059,189 A | 10/1991 | Cilento et al. | |
| 5,064,654 A | 11/1991 | Berner et al. | |
| 5,081,157 A | 1/1992 | Pomerantz | |
| 5,081,158 A | 1/1992 | Pomerantz | |
| 5,116,621 A | 5/1992 | Oji et al. | |
| 5,137,729 A | 8/1992 | Kuroya et al. | |
| 5,166,233 A | 11/1992 | Kuroya et al. | |
| 5,192,802 A | 3/1993 | Rencher | |
| 5,196,202 A | 3/1993 | Konishi | |
| 5,254,345 A | 10/1993 | Pogany et al. | |
| 5,254,346 A | 10/1993 | Tucker et al. | |
| 5,298,258 A | 3/1994 | Akemi et al. | |
| 5,314,915 A | 5/1994 | Rencher | |
| 5,332,576 A | 7/1994 | Mantelle | |
| 5,346,701 A | 9/1994 | Heiber et al. | |
| 5,462,749 A | 10/1995 | Rencher | |
| 5,466,465 A | 11/1995 | Royds et al. | |
| 5,505,956 A | 4/1996 | Kim et al. | |
| 5,516,523 A | 5/1996 | Heiber et al. | |
| 5,540,930 A | 7/1996 | Guy et al. | |
| 5,599,554 A * | 2/1997 | Majeti | 424/448 |
| 5,603,947 A * | 2/1997 | Wong et al. | 424/448 |
| 5,679,714 A * | 10/1997 | Weg | 514/647 |
| 5,700,478 A | 12/1997 | Biegajski et al. | |
| 5,723,143 A | 3/1998 | Jacques et al. | |
| 5,750,136 A | 5/1998 | Scholz et al. | |
| 5,780,047 A | 7/1998 | Kamiya et al. | |
| 5,800,832 A | 9/1998 | Tapolsky et al. | |
| 5,849,322 A | 12/1998 | Ebert et al. | |
| 5,853,760 A | 12/1998 | Cremer et al. | |
| 5,900,247 A | 5/1999 | Rault et al. | |
| 5,948,430 A | 9/1999 | Zerbe et al. | |
| 5,985,317 A | 11/1999 | Venkateshwaran et al. | |
| 6,159,498 A | 12/2000 | Tapolsky et al. | |
| 6,177,096 B1 | 1/2001 | Zerbe et al. | |
| 6,284,262 B1 | 9/2001 | Place | |
| 6,592,887 B2 | 7/2003 | Zerbe et al. | |
| 2005/0048102 A1 | 3/2005 | Tapolsky et al. | |

FOREIGN PATENT DOCUMENTS

| | | |
|---|---|---|
| EP | 0 050 480 | 4/1982 |
| EP | 0 159 604 | 10/1985 |
| EP | 0159604 A2 | 10/1985 |
| EP | 0 250 187 | 12/1987 |
| EP | 0 262 422 | 4/1988 |
| EP | 0275550 A1 | 7/1988 |
| EP | 0 381 194 | 8/1990 |
| EP | 0 654 261 A1 | 5/1995 |
| EP | 0 781 546 | 7/1997 |
| FR | 2497098 | 7/1982 |
| FR | 2582942 | 12/1986 |
| GB | 981372 | 1/1965 |
| GB | 2108841 | 5/1983 |
| JP | 56-100714 | 8/1981 |
| JP | 58-079916 | 5/1983 |
| JP | 60-116630 | 6/1985 |
| JP | 62-178513 | 2/1986 |
| JP | 61-280423 | 12/1986 |
| JP | 62-022713 | 1/1987 |
| JP | 62-056420 | 3/1987 |
| JP | 62-135417 | 6/1987 |
| JP | 63-060924 | 3/1988 |
| JP | 63-160649 | 7/1988 |
| JP | 63-310818 | 12/1988 |
| JP | 64-071812 | 3/1989 |
| JP | 64-090121 | 4/1989 |
| JP | 1-226823 | 9/1989 |
| JP | 3-246220 | 11/1991 |
| JP | 4-059723 | 2/1992 |
| JP | 9-504810 | 5/1997 |
| JP | 2001-508037 | 6/2001 |
| WO | WO-94/18925 A1 | 9/1994 |
| WO | WO-95/05416 | 2/1995 |
| WO | WO-95/05416 A2 | 2/1995 |
| WO | WO-9525544 | 9/1995 |

OTHER PUBLICATIONS

*Webster's New World Dictionary* (1988). V. Neufeldt ed. and D.B. Guralink ed., Prentice Hall: New York 3rd. College Ed., p. 505.

* cited by examiner

PHARMACEUTICAL CARRIER DEVICE SUITABLE FOR DELIVERY OF PHARMACEUTICAL COMPOUNDS TO MUCOSAL SURFACES

The instant application is a continuation of U.S. patent application Ser. No. 09/684,682, filed Oct. 4, 2000, which is a divisional of U.S. patent application Ser. No. 09/069,703, filed Apr. 29, 1998 which is a continuation-in-part application of PCT/US97/18605, filed Oct. 16, 1997, which is a PCT application claiming priority from Ser. No. 08/734,519, filed Oct. 18, 1996, which applications are incorporated herein by reference.

FIELD OF THE INVENTION

The present invention relates generally to a water-erodable pharmaceutical carrier which adheres to mucosal surfaces for the localized delivery of pharmaceutical compounds and protection of the treatment site.

BACKGROUND OF THE INVENTION

The localized treatment of body tissues, diseases, and wounds requires that the particular pharmaceutical component be maintained at the site of treatment for an effective period of time. Given the tendency of natural bodily fluids to rapidly wash away topically applied pharmaceutical components, the topical treatment of wet mucosal tissues has been problematic. In the mouth, saliva, natural replacement of the mucosal tissue, as well as, eating, drinking, and speaking movements are some of the problems that have limited the effectiveness and residence time of pharmaceutical carriers.

Bioadhesive carriers are known in the art and include gels, pastes, tablets, and films. These products, however, may lack one or several of the preferred characteristics for an efficient and commercially acceptable pharmaceutical delivery device. Some characteristics which are preferred by users of bioadhesive carriers include water-erodability; ease of handling and application to the treatment site; ease of comfort; minimal foreign body sensation; and unidirectional, specific release into the mucosal tissue. Other preferred characteristics for an effective and user-friendly product for the treatment of mucosal surfaces include the use of pharmaceutically approved components or materials; instantaneous adhesion to mucosal surface upon application; increased residence time for the protection of the affected tissue or the delivery of the pharmaceutical component; and ease of removal of the delivery device from the affected tissue or natural erosion of the delivery device at the delivery site.

Bioadhesive gels which are used for application to mucosal tissues and especially the oral cavity are known in the art. For example, U.S. Pat. No. 5,192,802 describes a bioadhesive teething gel made from a blend of sodium carboxymethyl cellulose and xanthan gum. The gel may also have potential use in the treatment of canker sores, fever blisters, and hemorrhoids. However, this type of pharmaceutical carrier has a very limited residence time, given that body fluids such as saliva quickly wash it away from the treatment site. Bioadhesive gels are also described in U.S. Pat. Nos. 5,314,915; 5,298,258; and 5,642,749. The gels described in those patents use an aqueous or oily medium and different types of bioadhesive and gelling agents.

Denture adhesive pastes are another type of bioadhesive product known in the art. However, these preparations are used primarily for their adhesive properties, to adhere dentures to the gums, rather than for the protection of tissue or for the topical delivery of is pharmaceuticals, although drugs such as local anesthetics may be used in the paste for the relief of sore gums. U.S. Pat. Nos. 4,894,232 and 4,518,721 describe denture adhesive pastes. The '721 patent describes a combination of sodium carboxymethyl cellulose and polyethylene oxide in polyethylene glycol.

Pastes have also been used as film protectants and as drug delivery systems. One such example having film forming and adhesive properties is the product commercialized under the name Orabase®-B, which is a thick gel or paste for the relief of mouth sores. Ingredients include guar gum, sodium carboxymethyl cellulose, tragacanth gum, and pectin. Even though it does provide numbing to the area of application, the film forming behavior and bioadhesion do not last. Thus, this product has a limited residence time.

Bioadhesive tablets are described in U.S. Pat. No. 4,915, 948. The water-soluble bioadhesive material used in this device is a xanthan gum or a pectin combined with an adhesion enhancing material such as a polyol. Although residence time is improved with the use of bioadhesive tablets, they are not user friendly, especially when used in the oral cavity, given the unpleasant feelings associated with their solidity, bulkiness, and slow erosion time.

Bioadhesive tablets are also described in U.S. Pat. Nos. 4,226,848; 4,292,299; and 4,250,163, and are single layer or bilayer devices having an average thickness of 0.2 to 2.5 mm. The bioadhesive tablets described in these patents utilize a non-adhesive component such as cellulose ether, a bioadhesive component such as polyacrylic acid, sodium carboxymethyl cellulose, or polyvinylpyrrolidone, and a binder for tableting purposes. The cellulose derivatives may or may not be water-erodable.

The use of bandages or bioadhesive laminated films, which are thinner and flexible and therefore have a decreased foreign body sensation, is described in U.S. Pat. Nos. 3,996,934 and 4,286,592. These products are used to deliver drugs through the skin or mucous. The laminated films usually include an adhesive layer, a reservoir layer, and a backing layer. Bioadhesive devices designed to release drug through the skin at a given rate and over a period of time are usually not water soluble, and thus are not dissolved or washed away by bodily fluids.

In addition to film systems for the delivery of drug through the skin, film delivery systems for use on mucosal surfaces are also known. These types of systems, which are water-insoluble and usually in the form of laminated, extruded or composite films, are described in U.S. Pat. Nos. 4,517,173; 4,572,832; 4,713,243; 4,900,554; and 5,137,729. The '173 patent describes and claims a membrane-adhering film consisting of at least three layers, including a pharmaceutical layer, a poor water soluble layer, and an intermediate layer. The pharmaceutical layer includes the drug and a cellulose derivative selected from hydroxypropyl cellulose, methyl cellulose, and hydroxypropyl methyl cellulose. The poor water soluble layer is made by the combination of one or more cellulose derivatives with a poor water soluble fatty acid, and the intermediate layer is made of cellulose derivatives. The '832 patent relates to a soft film for buccal delivery, made by the combined use of a water soluble protein, a polyol, and a polyhydric alcohol such as cellulose and polysaccharides, and also teaches the use of coloring or flavoring agents. The '243 patent describes a single or multi-layered bioadhesive thin film made from 40-95% water soluble hydroxypropyl cellulose, 5-60% water-insoluble ethylene oxide, 0-10% water-insoluble ethyl cellulose, propyl cellulose, polyethylene, or polypropylene, and a medicament. The films are three-layered laminates and include a bioadhesive layer, a reservoir layer, and a non water-soluble outer protective layer. The '729 patent teaches a soft adhesive film applicable to the oral mucosa containing a systemic drug and comprising a mixture of a vinyl acetate non water-soluble homopolymer, an acrylic acid polymer, and a cellulose derivative. Finally, the '554 patent describes a device for use in the oral cavity having an adhesive layer including a mixture of an acrylic acid polymer, a water-insoluble cellulose derivative, and a pharmaceutical preparation, and a water-insoluble or sparingly soluble backing layer. The adhesive layer contains the pharmaceutical, and upon application to the mucosal surface, delivers the drug. The '554 patent also states that "it is impossible to achieve an adhesive device for application to body tissue without all three components, that is, acrylic acid polymer, water insoluble cellulose derivative and a water insoluble or sparingly soluble backing layer."

JP 56-100714 describes a preparation which comprises a coating layer and an active ingredient layer. The coating layer adheres to the mucosal membrane and is comprised of a cellulose ether or an acrylic acid polymer or salt. The active ingredient layer comprises an ointment base comprised of water-insoluble substances such as fats and oils, waxes, hydrocarbons, higher fatty acids, higher alcohols, polyhydric alcohols or glycerol esters. A surfactant and active ingredient are also present in the active ingredient layer. Thus, the active ingredient is mixed with an essentially non-water erodable substance. The previous examples of thin films to be applied in the oral cavity by adhesion onto the mucosal tissues all utilize polymers which are water-insoluble by nature or which are made water-insoluble by crosslinking, and claim a long residence time. Therefore, unfortunately, the above examples of thin films do not provide a water erodable device with good adhesive properties. Therefore, upon release of the desired amount of drug, the thin films of water insoluble polymers must be peeled off the site of application. Such peeling often removes tissue from the mucosal tissue and is painful to the patient. What is needed in the art is a water-erodable pharmaceutical delivery device which provides good adhesion and localized delivery of a pharmaceutical with minimal discomfort to the patient.

SUMMARY OF THE INVENTION

The present invention relates to a novel water-erodable pharmaceutical carrier device for application to mucosal surfaces to provide protection of and localized delivery of pharmaceutical to the site of application, surrounding tissues, and other bodily fluids such as blood or lymph, having an effective residence time, with minimal discomfort and ease of use. In one embodiment, the pharmaceutical delivery device includes a layered film disk which is water-erodable. The device comprises a layered film disk having an adhesive layer and a backing layer, both water-erodable, having the pharmaceutical in one or more of the layers.

In another embodiment, the pharmaceutical delivery device further comprises a third layer between the first adhesive layer and the second backing layer. The third layer is a water-erodable adhesive layer which has a surface area sufficient to encompass said first adhesive layer and contact the mucosal surface. In this manner, localized delivery of a pharmaceutical may be accomplished in a unidirectional manner toward the mucosal layer.

The adhesive layer(s) comprise(s) a film-forming polymer such as hydroxyethyl cellulose, hydroxypropyl cellulose, hydroxypropylmethyl cellulose, hydroxyethyl methyl cellulose, polyvinyl alcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin, or chitosan, alone or in combination and a bio-adhesive polymer such as polyacrylic acid, polyvinyl pyrrolidone, or sodium carboxymethyl cellulose, alone or in combination.

The non-adhesive backing layer(s) comprise(s) hydroxyethyl cellulose, hydroxypropyl cellulose, hydroxyethylmethyl cellulose, hydroxypropylmethyl cellulose, polyvinyl alcohol, polyethylene glycol, polyethylene oxide, or ethylene oxide-propylene oxide co-polymers, alone or in combination.

In another embodiment of the invention, one or more of the layers of the device further comprise a component which acts to adjust the kinetics of the erodability and provide a convenient manner of altering the release of the pharmaceutical and the lifespan of the device. A component which acts to adjust the kinetics of the erodability is a water-based emulsion of a polylactide, polyglycolide, lactide-glycolide copolymers, poly-ε-caprolactone and derivatives, polyorthoesters and derivatives, polyanhydrides and derivatives, ethyl cellulose, vinyl acetate, cellulose acetate, and polyisobutylene, alone or in combination. Another component which acts to adjust the kinetics of the erodability is alkyl-glycol, propylene glycol, polyethyleneglycol, oleate, sebacate, stearate or esters of glycerol, or phthalate, alone or in combination.

In another embodiment of the invention, the number of layers of the device further may be varied to adjust the kinetics of the erodability and provide a convenient manner of altering the release of the pharmaceutical and the lifespan of the device.

In a preferred embodiment, the backing layer comprises two or more layers with different erodibility kinetics.

DETAILED DESCRIPTION OF THE INVENTION

As used herein, the term "water-erodable" means that the component, device, layer, etc. erodes in water-based media such as saliva, over time. Such erosion in water may be due to factors such as dissolution, dispersion, friction, gravity, etc.

As used herein, the term "kinetics of erodability" or "erosion kinetics" refers to the timing of the release of pharmaceutical from the carrier device (release profile), as well as, the timing of the erosion of the device itself over time (lifespan or residence time of the device). As described herein, kinetics of erodability are based on factors such as type and amount of components in the device, thickness and number of layers in the device, and additives or excipients in the device. In a case in which all the components of the device are very water soluble, the kinetics of erodability will closely parallel the solubility kinetics.

In the present invention, a novel water-erodable pharmaceutical device which adheres to mucosal surfaces is provided. The present invention finds particular use in the localized treatment of body tissues, diseases, or wounds which may have moist surfaces and which are susceptible to bodily fluids, such as the mouth, the vagina, or other types of mucosal surfaces. The device carries a pharmaceutical, and upon application and adherence to the mucosal surface, offers a layer of protection and delivers the pharmaceutical to the treatment site, the surrounding tissues, and other bodily fluids. The device provides an appropriate residence time for effective drug delivery at the treatment site, given the control of erosion in aqueous solution or bodily fluids such as saliva, and the slow, natural erosion of the film concomitant or subsequent to the delivery. In one embodiment, the pharmaceutical delivery device comprises a layered film disk having an adhesive layer and a backing layer, both water-erodable, having the pharmaceutical in either or both layers.

Unlike bioadhesive gels and pastes known in the art, which have a very limited residence time, given the tendency of bodily fluids such as saliva to wash away the gel from the treatment site, the present invention offers an increased residence time because of its filmy consistency and components. A typical residence time for an aqueous gel or paste, such as Orajel®, Orabase®, or Kanka® is a few minutes. This short residence time is a consequence of a limited or poor adhesion. In a typical aqueous gel, the mucoadhesive components are either in solution, suspension, or swollen. Once applied to the mucosal surface, however, the water based gel does not instantaneously penetrate the lipophilic mucosal surface. The composition and water affinity of these gels results in a tendency to quickly mix with the saliva, rapidly pulling away the different components of the gel, and limiting the residence time. The same tendency is expected with pastes, the increase in viscosity only slightly delaying the timing. The present invention, by its solid form and its instantaneous adhesion to the mucosal surface, allows a lasting contact, a consequence of the entanglement of polymer chains and glycoproteins of the mucosal tissue which assures adhesion. Erosion kinetics in the saliva and other aqueous media are influenced by the physical state of the device. While a gel or solution will readily mix with saliva and/or other bodily fluids, a solid form of the same or similar composition, such as the film of the present invention, dissolves/erodes more slowly.

Also, unlike the bioadhesive tablets which are known in the art, the pharmaceutical device of the present invention minimizes the discomfort associated with application of a foreign substance for a period of time sufficient to provide effective drug delivery to the treatment site. Often, users of the bioadhesive tablets of the prior art experience unpleasant sensations due to their solidity, bulkiness, and slow dissolution time if erodable, especially when used in the oral cavity. Moreover, the typical thickness of bioadhesive tablets, which may or may not be water soluble, is a couple of millimeters, and because of their thickness, the preferred site of application is on the upper gingival area. This site is usually unsatisfactory for local delivery as the type of compounds to be delivered, their bioavailability, and pharmokinetics is limited. In contrast to tablets, the device of the present invention offers the advantages of an effective residence time with minimal discomfort and ease of use, and is an appropriate vehicle for the local, as well as systemic, delivery of pharmaceutical, given its thinner, flexible form.

Finally, unlike the film systems known in the art which are used to deliver pharmaceutical through the skin or mucous, the device of the present invention is made of water-erodable components and thus is bioerodable. The use of water-erodable components allows the device to erode over a period of time, with natural bodily fluids slowly dissolving or eroding away the carrier, while the pharmaceutical remains at the application site. Unlike bandages and other non-water-erodable film systems, the user of the present invention does not have to remove the device following treatment. Nor does the user experience the sensation of the presence of a foreign object at the mucosal surface or within the body cavity, given that upon application, water absorption softens the device, and over time, the device slowly dissolves or erodes away.

The residence time of the device of the present invention depends on the erosion rate of the water erodable polymers used in the formulation and their respective concentrations. The erosion rate may be adjusted, for example, by mixing together components with different solubility characteristics or chemically different polymers, such as hydroxyethyl cellulose and hydroxypropyl cellulose; by using different molecular weight grades of the same polymer, such as mixing low and medium molecular weight hydroxyethyl cellulose; by using excipients or plasticizers of various lipophilic values or water solubility characteristics (including essentially insoluble components); by using water soluble organic and inorganic salts; by using crosslinking agents such as glyoxal with polymers such as hydroxyethyl cellulose for partial crosslinking; or by post-treatment irradiation or curing, which may alter the physical state of the film, including its crystallinity or phase transition, once obtained. These strategies might be employed alone or in combination in order to modify the erosion kinetics of the device.

Upon application, the pharmaceutical delivery device adheres to the mucosal surface and is held in place. Water absorption softens the device, thereby diminishing the foreign body sensation. As the device rests on the mucosal surface, delivery of the drug occurs. Residence times may be adjusted over a wide range depending upon the desired timing of the delivery of the chosen pharmaceutical and the desired lifespan of the carrier. Generally, however, the residence time is modulated between about a few seconds to about a few days. Preferably, the residence time for most pharmaceuticals is adjusted from about 30 minutes to about 24 hours. More preferably, the residence time is adjusted from about 1 hour to about 8 hours. In addition to providing drug delivery, once the device adheres to the mucosal surface, it also provides protection to the treatment site, acting as an erodable bandage.

In one embodiment, the present invention comprises a film disc having an adhesive layer and a non-adhesive backing layer which can be comprised of components having a similar or different hydrophilicity. The pharmaceutical component may be included in either layer, although preferably, it is included in the adhesive layer, which is closest to the treatment site and which will have a slower erosion time, given that the backing layer protects the interior, adhesive layer and will typically erode first.

The adhesive layer may comprise at least one film-forming water-erodable polymer (the "film-forming polymer") and at least one pharmacologically acceptable polymer known for its bioadhesive capabilities (the "bioadhesive polymer"). The film forming polymer may comprise hydroxyethyl cellulose, hydroxypropyl cellulose, hydroxypropylmethyl cellulose, hydroxyethyl methyl cellulose, polyvinyl alcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin and chitosan, alone or in combination. Preferably, the film-forming polymer comprises hydroxyethyl cellulose and hydroxypropyl cellulose. Preferably, in the case of hydroxyethyl cellulose, the average molecular weight (Mw estimated from intrinsic viscosity measurements) is in the range $10^2$ to $10^6$ and more preferably in the range $10^3$ to $10^5$, while in the case of hydroxypropyl cellulose, the average molecular weight (Mw obtained from size exclusion chromatography measurements) is in the range $50\times10^3$ to $1.5\times10^6$, and more preferably between $80\times10^3$ to $5\times10^5$.

The bioadhesive polymer of the adhesive layer may comprise polyacrylic acid (PAA), which may or may not be partially crosslinked, sodium carboxymethyl cellulose (NaCMC), and polyvinylpyrrolidone (PVP), or combinations thereof. These bioadhesive polymers are preferred because they have good and instantaneous mucoadhesive properties in a dry, film state. In the case of sodium carboxymethyl cellulose, typical average molecular weights comprise 50,000 to 700,000, and preferably 60,000 to 500,000, with a degree of substitution of 0.7. The substitution range varies between 0.5 and 1.5, and preferably between 0.6 and 0.9. The polyvinyl pyrrolidone can be characterized according to its average molecular weight and comprises between 5,000 and 150,000, preferably between 10,000 and 100,000. The simultaneous use of PAA with some grades of PVP may result in the precipitation of one or both components. This precipitation may not be ideal to obtain a homogenous layer and may slightly alter the overall adhesive properties of the device.

While not wishing to bound to a particular theory, it is believed that the adhesion properties of the present invention are the result of the entanglement of polymer chains and interactions with glycoproteins of the mucosal surface. The chemical nature of the bioadhesive polymers, including chain and side groups and crosslinking agents, generates interactions between the mucosal constituents and the polymer or polymers, such as physical entanglement, Van der Waals interactions, and hydrogen bonding. Given that the composition of mucosal tissues differs from one individual to another and changes naturally over time, the use of a combination of bioadhesive polymers or the use of a combination of different grades of the same polymer is preferred. The use of a combination of at least two bioadhesive polymers maximizes the adhesion capabilities of the device, although use of a single bioadhesive polymer is effective as well.

The ratio of the bioadhesive polymer to the film-forming polymer in the adhesive layer may vary, depending on the type of pharmaceutical and the amount of pharmaceutical to be used. However, the content of combined components in the adhesive layer is usually between 5 and 95% by weight, preferably between 10 and 80% by weight. In terms of weight percent of the different bioadhesive polymers PAA, NaCMC, and PVP, some examples are provided below and using the examples one skilled in the art will be able to readily adjust the percentages to obtain a pharmaceutical device having desired characteristics for a given application. Preferred combinations include PAA and NaCMC, NaCMC and PVP, or PAA and PVP, and also include the use of different grades of the same polymer.

The non adhesive backing layer may comprise a water-erodable, film-forming pharmaceutically acceptable polymer such as hydroxyethyl cellulose, hydroxypropyl cellulose, hydroxypropylmethyl cellulose, hydroxyethylmethyl cellulose, polyvinylalcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin and chitosan, alone or in combination. The backing layer component may or may not be crosslinked depending on the desired erosion kinetics. In one embodiment, the preferred backing layer component comprises hydroxyethyl cellulose or hydroxypropyl cellulose, and more preferably comprises hydroxyethyl cellulose. Preferably, in the case of hydroxyethyl cellulose, the average molecular weight (Mw estimated from intrinsic viscosity measurements) is in the range $10^2$ to $10^6$, and more preferably in the range $10^3$ to $10^5$, while in the case of hydroxypropyl cellulose, the average molecular weight (Mw obtained from size exclusion chromatography measurements) is in the range of $50\times10^3$ to $1.5\times10^6$ and more preferably from $80\times10^3$ to $5\times10^5$.

Moreover, it has been discovered that a particularly preferable combination for the backing layer comprises hydroxypropyl cellulose and an alkylcellulose such as is methylcellulose or ethylcellulose. Such a combination comprises a film-forming amount of alkylcellulose, hydroxypropyl cellulose, and a suitable solvent. Advantageously, the characteristics of the film formed from the gel may be modified depending upon the ratio of hydroxypropyl cellulose to alkylcellulose. Such modifiable characteristics advantageously include the kinetics of erodability.

Typically, the ratio of hydroxypropyl cellulose to alkylcellulose is that necessary to form a suitable film. This ratio may vary based on the other components and the type of alkylcellulose. However, if ethylcellulose is employed then the ratio of hydroxypropyl cellulose to ethyl cellulose is usually from about 1000:1 to about 3:1, preferably from about 200:1 to about 4:1, more preferably from about 200:1 to about 8:1. Typically, as the ratio of hydroxypropyl cellulose to alkylcellulose increases, the water erodability increases, i.e., the films are more readily washed away. Thus, the ethylcellulose is a component which acts to adjust the kinetics of erodability of the device.

As described above, the erosion kinetics of one or more of the layers (adhesive layer, backing layer, or both) may be altered in many different ways in order to modify the residence time and the release profile of a drug. One way is by crosslinking or plasticizing the film-forming polymer. Crosslinking agents known in the art are appropriate for use in the invention and may include glyoxal, propylene glycol, glycerol, dihydroxy-polyethylene glycol of different sizes, butylene glycol, and combinations thereof. The amount of crosslinking agent used may vary, depending on the particular polymers and crosslinking agent but usually should not exceed 5% molar equivalent of the polymeric material, and preferably comprises 0 to 3% molar equivalent of the polymeric material.

Another way of altering the residence time and release profile is by employing a component in one or more of the layers which acts to adjust the kinetics of the erodability of the layer. While these components will vary widely depending upon the particular pharmaceutical delivery device employed, preferred components include water-based emulsions of polylactide, polyglycolide, lactide-glycolide copolymers, poly-ϵ-caprolactone and derivatives, polyorthoesters and derivatives, polyanhydrides and derivatives, ethyl cellulose, vinyl acetate, cellulose acetate, silicone, polyisobutylene and derivatives, alone or in combination.

It is also possible to adjust the kinetics of erodability of the devices by adding excipients which are very soluble in water such as water soluble organic and inorganic salts. Suitable such excipients may include the sodium and potassium salts of chloride, carbonate, bicarbonate, citrate, trifluoroacetate, benzoate, phosphate, fluoride, sulfate, or tartrate. The amount added will vary depending upon how much the erosion kinetics are to be altered as well as the amount and nature of the other components in the device.

Emulsifiers typically used in the water-based emulsions described above are, preferably, either obtained in situ if selected from the linoleic, palmitic, myristoleic, lauric, stearic, cetoleic or oleic acids and sodium or potassium hydroxide, or selected from the laurate, palmitate, stearate, or oleate esters of sorbitol and sorbitol anhydrides, polyoxyethylene derivatives including monooleate, monostearate, monopalmitate, monolaurate, fatty alcohols, alkyl phenols, alyl ethers, alkyl aryl ethers, sorbitan monostearate, sorbitan monooleate and sorbitan monopalmitate.

Furthermore, in the case of the water-insoluble polymeric materials such as the polyesteraliphatic family (co-polymers of lactide-glycolide, caprolactone, etc.) the average molecular weight (Mw) is in the range $10^2$ to $10^5$ and, more preferably, $10^3$ to $10^4$, while in the case of the cellulosic family (ethyl cellulose, cellulose acetate, etc.), the average molecular weight (Mw estimated from intrinsic viscosity measurements) is in the range $10^2$ to $10^6$ and more preferably in the range $10^3$ to $10^5$.

Yet another manner of modifying the erosion kinetics of any layer, is by employing excipients which plasticize the film concomitantly. The excipient or plasticizer often improves the mechanical properties of the device and/or modifies the drug release profile or disintegation time. Suitable excipients or plasticizers modifying the erosion behavior of the layer(s) may include alkyl-glycol such as propylene glycol, polyethyleneglycols, oleate, sebacate, stearate or esters of glycerol, phthalate and others. Other suitable plasticizers include esters such as acetyl citrate, amyl oleate, myristyl acetate, butyl oleate and stearate, dibutyl sebacate, phthalate esters such as diethyl, dibutyl, and diethoxy ethyl phthalate and the like, fatty acids such as oleic and stearic acid, fatty alcohols such as cetyl, myristyl, and stearyl alcohol. Moreover, in some instances, a polymer, a pharmaceutical, or solvent residual may act as a plasticizer.

It is also possible to modify the erosion kinetics of the device of the instant invention by adjusting the thickness and number of layers. Typically, the thicker the layers, the slower the release of pharmaceutical and the longer the release profile. Correspondingly, the more layers there are, the slower the release of pharmaceutical and the longer the release profile. In a preferred embodiment, the backing layer comprises two or more layers with different erosion kinetics.

Moreover, combinations of different polymers or similar polymers with definite molecular weight characteristics may be used in order to achieve preferred film forming capabilities, mechanical properties, and kinetics of dissolution in any layer. Some combinations for use in the invention are provided in the examples below and may include ¾ of hydroxyethyl cellulose and ¼ of hydroxypropyl cellulose; ⅘ of low molecular weight hydroxyethyl cellulose and ⅕ of medium molecular weight hydroxyethyl cellulose; and ⅚ of low molecular weight hydroxyethyl cellulose and ⅙ of high molecular weight hydroxyethyl cellulose. As mentioned previously, combinations of water-erodable polymers may be employed in order to modify the erosion kinetics of the device. A particularly preferred combination includes ½ hydroxyethyl cellulose, ⅙ hydroxypropylcellulose, and ⅔ of a pseudolatex, i.e. emulsion of polymer, of lactide-glycolide copolymer.

The pharmaceutical component of the present invention may comprise a single pharmaceutical or a combination of pharmaceuticals, which may be incorporated in the adhesive layer, the backing layer, or both. Pharmaceuticals which may be used, either alone or in combination, include anti-inflammatory analgesic agents, steroidal anti-inflammatory agents, antihistamines, local anesthetics, bactericides and disinfectants, vasoconstrictors, hemostatics, chemotherapeutic drugs, antibiotics, keratolytics, cauterizing agents, antiviral drugs, antirheumatics, antihypertensives, bronchodilators, anticholinergics, antimenimic compounds, hormones and macromolecules, peptides, proteins and vaccines.

Examples of anti-inflammatory analgesic agents include acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc. Examples of steroidal anti-inflammatory agents include hydrocortisone, predonisolone, dexarnethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, etc.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc. Examples of local anesthetics include dibucaine hydrochloride, dibucaine, lidocaine hydrochloride, lidocaine, benzocaine, p-buthylaminobenzoic acid 2-(diethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iode, cetylpyridinium chloride, eugenol, trimethylammonium bromide, etc. Examples of vasoconstrictors include naphazoline nitrate, tetrahydrozoline hydrochloride, oxymetazoline hydrochloride, phenylephrine hydrochloride, tramazoline hydrochloride, etc. Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitrofurazone, etc. Examples of antibiotics include penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, cycloserine, etc.

Examples of keratolytics include salicylic acid, podophyllum resin, podolifox, and cantharidin. Examples of cauterizing agents include the chloroacetic acids and silver nitrate. Examples of antiviral drugs include protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Examples of proteins, peptides, vaccines, genes and the like include heparin, insulin, LHRH, TRH, interferons, oligonuclides, calcitonin, and octreotide.

Other pharmaceuticals which may be employed include omeprazone, fluoxetine, ethinylestradiol, amiodipine, paroxetine, enalapril, lisinopril, leuprolide, prevastatin, lovastatin, norethindrone, risperidone, olanzapine, albuterol, hydrochlorothiazide, pseudoephridrine, warfarin, terazosin, cisapride, ipratropium, busprione, methylphenidate, levothyroxine, zolpidem, levonorgestrel, glyburide, benazepril, medroxyprogesterone, clonazepam, ondansetron, losartan, quinapril, nitroglycerin, midazolam versed, cetirizine, doxazosin, glipizide, vaccine hepatitis B, salmeterol, sumatriptan, triamcinolone acetonide, goserelin, beclomethasone, graniseteron, desogestrel, alprazolam, estradiol, nicotine, interferon beta 1A, cromolyn, fosinopril, digoxin, fluticasone, bisoprolol, calcitril, captorpril, butorphanol, clonidine, premarin, testosterone, sumatriptan, clotrimazole, bisacodyl, dextromethorphan, nitroglycerine In D, nafarelin, dinoprostone, nicotine, bisacodyl, goserelin, and granisetron.

The amount of active pharmaceutical (s) to be used depends on the desired treatment strength and the composition of the layers, although preferably, the pharmaceutical component comprises from about 0.001 to about 99, more preferably from about 0.003 to about 30, and most preferably from about 0.005 to about 20% by weight of the device.

Plasticizers, flavoring and coloring agents, and preservatives may also be included in the pharmaceutical delivery device of the present invention in the adhesive layer, the backing layer, or both. The amounts of each may vary depending on the drug or other components but typically these components comprise no more than 50, preferably no more than 30, most preferably no more than 15% by total weight of the device.

A permeation enhancer may be added to the device to improve absorption of the drug. Typically, such a permeation enhancer is added to the layer in which the pharmaceutical is to be contained. Suitable permeation enhancers include natural or synthetic bile salts such as sodium fusidate; glycocholate or deoxycholate; fatty acids and derivatives such as sodium laurate, oleic acid, oleyl alcohol, monoolein, and palmitoylcarnitine; chelators such as disodium EDTA, sodium citrate and sodium laurylsulfate, azone, sodium cholate, sodium 5-methoxysalicylate, sorbitan laurate, glyceryl monolaurate, octoxynonyl-9, laureth-9, polysorbates, etc.

The thickness of the device may vary, depending on the thickness of each of the layers and the number of layers. As stated above, both the thickness and amount of layers may be adjusted in order to vary the erosion kinetics. Preferably, if the device has only two layers, the thickness ranges from 0.05 mm to 3 mm, preferably from 0.1 to 1 mm, and more preferably from 0.1 to 0.5 mm. The thickness of each layer may vary from 10 to 90% of the overall thickness of the layered device, and preferably varies from 30 to 60%. Thus, the preferred thickness of each layer may vary from 0.01 mm to 0.9 mm, and more preferably from 0.03 to 0.6 mm.

While the device of the invention only requires two layers, i.e., an adhesive layer and a backing layer, it is often preferable to have additional layers. One instance in which this might be advantageous is when specific unidirectional flow of a pharmaceutical is required is toward a mucosal layer. The layered device described above provides some directional release, i.e., release will mainly be toward the mucosa and not, for instance, into the oral or vaginal cavity. However, due to the swelling characteristics of the thin film, a small amount of pharmaceutical may also be released through the sides of the device and the backing layer if all the layers are of the approximately the same surface area and are essentially on top of one another. While a preferential, but not specific, release is acceptable, and even desirable, for many pharmaceuticals, other pharmaceuticals may require unidirectional, specific release into the mucosal tissue.

An example of when unidirectional release may be desirable is when the pharmaceutical to be delivered has a specific therapeutic window or has undesirable side effects if absorbed in the gastrointestinal tract. Furthermore, some pharmaceuticals are enzymatically degraded. Therefore, a bioerodible mucoadhesive system allowing a transmucosal unidirectional delivery and protecting the drug being delivered from enzymes present, for instance, in the oral or vaginal cavities would have advantages.

Figure 1:
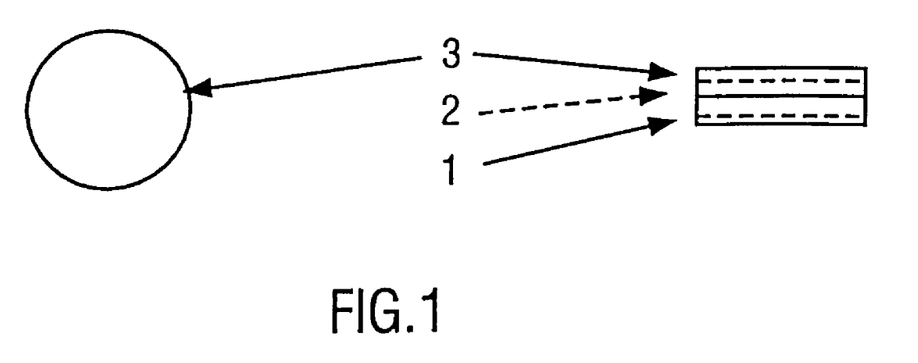
FIG. 1 is a three layered film disk wherein layers 2 and 3 are bioadhesive layers and layer 1 is a backing layer.
Figure 2:
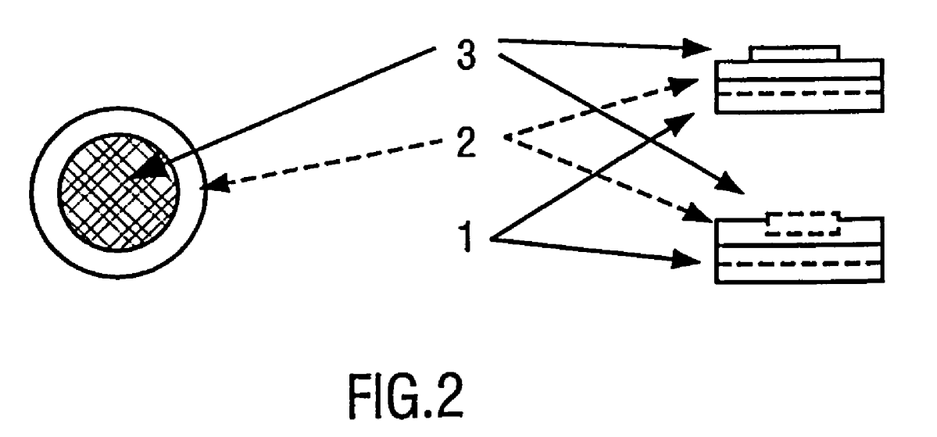
FIG. 2 is a three layered film disk wherein two of the layers are bioadhesive layers and the other layer is a backing layer. The bioadhesive layer, layer 3, which will adhere to the mucosal tissue is of smaller surface area and encompassed by the second bioadhesive layer, layer 2, to provide unidirectional delivery. Layer 1 is a backing layer.

In such instances when unidirectional release is desired, an additional layer may be placed between the first adhesive layer and the second backing layer. The third layer is a water-erodable adhesive layer which has a surface area sufficient to encompass said first adhesive layer and contact the mucosal surface. The third layer may be comprised of any of the components described above for the first adhesive layer and thus may be the same or different than the first adhesive layer. FIG. 2 illustrates a disk having a third layer which encompasses the first adhesive layer.

If a bioadhesive layer is to be of a smaller surface area than the other layers then it is usually between about 5 and about 50, preferably between about 10 and about 30% smaller than the other layers.

In the aforementioned manner, localized delivery of a pharmaceutical may be accomplished in a unidirectional manner. For instance, if pharmaceutical is present in the first adhesive layer then it is prevented from being released through the sides and back of the device. If pharmaceutical is present in the backing layer, then it is prevented from entering is the mucosal layer to which the device is adhered. Likewise, if a pharmaceutical is present in the first adhesive layer and the backing layer, they are prevented from mixing.

The pharmaceutical delivery device of the present invention may be prepared by numerous methods known in the art. In one embodiment, the components are dissolved in a biocompatible solvent, preferably an aqueous medium or a combination of water and lower alkanols, to prepare a solution, a gel, or a suspension that can be used for coating. Solvents for use in the present invention may comprise water, methanol, ethanol, propanol, or low alkyl alcohols such as isopropyl alcohol, or acetone. Other suitable solvents may comprise dimethyl acetamide, N-methyl-2-pyrrolidone, dimethyl sulfoxide, ethoxydiglycoli, propylene glycol, polyethylene glycol. The final solvent content or residual solvent content in the film may be the result of either or both layers. Typically, such final solvent content is at least about 10, preferably at least about 5, more preferably at least about 1% by weight of the total device. Similarly, the final solvent content is not more than about 20, preferably not more than about 15, most preferably not more than about 10% by weight of the total device. The solvent may also be used as a plasticizer or an erosion rate-modifying agent.

Each solution is then coated onto a substrate. Eventually, one of the components might be in suspension. Each solution is casted and processed into a thin film by techniques known in the art, such as by film dipping, film coating, film casting, spin coating, or spray drying using the appropriate substrate. The thin film is then allowed to dry. If desired, the drying step can be accomplished in any type of oven in order to facilitate the process. However, as one skilled in the art will appreciate, the solvent residual, which may effect the erosion kinetics, depends on the drying procedure. The film layers may be filmed independently and then laminated together or may be filmed one on the top of the other.

The film obtained after the two layers have been laminated together or coated on top of each other may be cut, if desired, into any type of shape which is suitable for application to the mucosal tissue. Suitable shapes may include disks, ellipses, squares, rectangles, parallepipedes, as well as, shredded, meshed, or porous films depending upon the purpose and location where the device is to be employed. Likewise, the surface area of the device of the present invention will necessarily vary depending on many factors with the major factor being where the device is to be employed. Typically, the surface area may be from about 0.1 to about 30, preferably from 0.5 to about 20 square centimeters.

Methods for treating mucosal surfaces, surrounding tissues, and bodily fluids for localized and systemic drug delivery are also provided. In one embodiment, the method comprises applying an adherent film of the invention to the treatment site in order to provide protection to the treatment site and drug delivery. The adherent film may comprise any of the layered devices provided herein. In a preferred embodiment, the method comprises application of a layered pharmaceutical carrier device having a first adhesive layer and a second non-adhesive backing layer as described above, each layer having a thickness of from 0.01 mm to 0.9 mm. The pharmaceutical or combination of pharmaceuticals may be present in the adhesive layer, the non-adhesive backing layer, or both layers.

As one skilled in the art will appreciate, when systemic delivery. e.g., transmucosal or transdermal delivery, is desired the treatment site may include any area in which the adherent film of the invention is capable of maintaining a desired level of pharmaceutical in the blood, lymph, or other bodily fluid. Typically, such treatment sites include the oral, anal, nasal, and vaginal mucosal tissue, as well as, the skin. If the skin is to be employed as the treatment site, then usually larger areas of the skin wherein movement will not disrupt the adhesion of the device, such as the upper arm or thigh, are preferred.

While the pharmaceutical carrier described in this application readily adheres to mucosal tissues, which are wet tissues by nature, it can also be used on other surfaces such as skin or wounds. The water-soluble film of the present invention will adhere to the skin if prior to application the skin is wet with an aqueous-based fluid such as water, saliva, or perspiration. The film will typically adhere to the skin until it erodes due contact with water by, for example, showering, bathing or washing. The film may also be readily removed by peeling without significant damage to tissue.

While it is in contact with the skin, the film may act as a washable, erodable bandage to protect the area where it has been applied. It is also possible to employ the film as a transdermal drug delivery system to facilitate the healing process and keep the wound or burn free of germs and debris. A significant advantage of the instant invention over conventional alternatives is that not only is the film washable, but also, perspiration helps the adhesion of the device instead of preventing or reducing it as with conventional transdermal patches.

The pharmaceutical carrier of the present invention can also be used as a wound dressing. By offering a physical, compatible, oxygen and moisture permeable, flexible barrier which can be washed away, the film can not only protect a wound but also deliver a pharmaceutical in order to promote healing, asepty, scarification, to ease the pain or to improve globally the condition of the sufferer. Some of the: examples given below are well suited for an application to the skin or a wound. As one skilled in the art will appreciate, the formulation might require incorporating a specific hydrophilic/hygroscopic excipient which would help in maintaining good adhesion on dry skin over an extended period of time. Another advantage of the present invention when utilized in this manner is that if one does not wish that the film be noticeable on the skin, then no dyes or colored substances need be used. If, on the other hand, one desires that the film be noticeable, a dye or colored substance may be employed.

The following examples are provided to illustrate pharmaceutical carrier devices, as well as, methods of making and using, pharmaceutical carrier devices of the present invention.

EXAMPLE 1

A 100 ml solution for the non-adhesive backing layer was made using 87.98% by weight water USP, 0.02% by weight FD&C red 40 dye, and 12% by weight hydroxyethyl cellulose (Mw $9 \times 10^4$). Using a Werner Mathis Labcoater, the substrate (Mylar 1000D or other polyester films such as 3M ScotchPak 1022) was set. 90 ml of the backing layer solution was set in front of a knife over roll with an opening of 1.5 mm. The solution was then casted and the film dried for 8-9 min. at 60° C. Following the drying step, a 0.14 mm thick reddish film was the result.

Using this procedure, the film may be easily peeled off the substrate after drying, or may be left on the substrate and rolled, to be laminated later, or for use as a substrate for the adhesive layer.

EXAMPLE 2

A 100 ml solution for the non-adhesive backing layer was made using 94.98% by weight water USP, 0.02% by weight FD&C red 40 dye, and 5% by weight hydroxypropyl cellulose. The procedure of example 1 was used, resulting in a 0.16 mm thick film.

EXAMPLE 3

A 100 ml solution for the non-adhesive backing layer was made using 84.98% by weight water USP, 0.02% by weight FD&C red 40 dye, 12% by weight hydroxyethyl cellulose, and 3% by weight hydroxypropyl cellulose. Here, the overall polymeric material was at a 15% concentration in solution. The mixture of two different types of polymeric materials modified the overall mechanical properties and erosion kinetics characteristics of the backing film. The solution was then casted on a polyester substrate and dried overnight at 90° C. The opening of the knife was set at 3 mm, resulting in a 0.3 mm thick film.

EXAMPLE 4

A 100 ml solution for the non-adhesive backing layer was made using 87.98% by weight water USP, 0.02% by weight FD&C red 40 dye, 10% by weight hydroxyethyl cellulose (Mw $9 \times 10^4$), and 2% by weight hydroxyethyl cellulose (Mw $7 \times 10^5$). Here, the mixture of two different types of hydroxyethyl cellulose modified the mechanical properties and erosion kinetics of the backing film. The solution was then cast on a polyester substrate and dried for 12 min. at 135° C. The opening of the knife was set at 3 mm, resulting in a 0.27 mm thick film.

EXAMPLE 5

A 100 ml solution for the non-adhesive backing layer was made using 87.98% by weight water USP, 0.02% by weight FD&C red 40 dye, 11.75% by weight hydroxyethyl cellulose (Mw $9 \times 10^4$), and 0.25% by weight hydroxyethyl cellulose (Mw $1.3 \times 10^6$). The procedure of Example 1 was used, resulting in a 0.14 mm thick film.

Here, the mixture of two different grades of hydroxyethyl cellulose modified the mechanical properties and erosion kinetics of the backing film. The ratio may be used to adjust the erosion pattern and residence time of the bioadhesive disk. Compared to the backing layer of Example 1, which was made of 12% by weight hydroxyethyl cellulose (Mw $9 \times 10^4$), and which had an erosion time of about 21 minutes (See Table 2), the backing layer of this Example, made from a combination of two grades of hydroxyethyl cellulose, had an erosion time of about 69 minutes (See Table 2).

EXAMPLE 6

A 100 ml solution for the non-adhesive backing layer was made using 87.98% by weight water USP, 0.02% by weight FD&C red 40 dye, 11.95% by weight hydroxyethyl cellulose (Mw $9 \times 10^4$), and 0.05% by weight of 40% glyoxal aqueous solution. The procedure of Example 1 was used, resulting in a 0.13 mm film.

Here, the glyoxal acted as a crosslinking agent, inducing a slow down in the erosion kinetics of the backing film. Compared to the backing layer of Example 1, which had no glyoxal and which had an erosion time of about 21 minutes (See Table 2), the backing layer of this Example, which incorporated glyoxal, had an erosion time of about 57 minutes (See Table 2).

EXAMPLE 7

A 100 ml solution for the non-adhesive backing layer was made using 87.98% by weight water USP, 0.02% by weight FD&C red 40 dye, 11.8% by weight hydroxyethyl cellulose, 0.1% by weight of 40% glyoxal aqueous solution, and 0.1% sweet peppermint flavor. Here, as in Example 6, the glyoxal acted as a crosslinking agent, inducing a slow down in the erosion kinetics of the backing film, compared with a backing layer with no glyoxal. The sweet peppermint was added as a flavoring agent.

EXAMPLE 8

As described in Example 1, the solutions of Examples 5, 6 and 7 were each casted on a polyester substrate. Instead of using a knife, a meier's bar was used to coat the substrate. The films were dried overnight at 90° C. The dried films were thicker, having a thickness of about 0.17 mm.

EXAMPLE 9

The solution of Example 1 was prepared in a beaker. A microslide was then dipped quickly into the solution until it was fully immersed, removed from the solution, and left at room temperature for about 1 hour. The microslide was then dried overnight at 90° C. The resulting film was heterogeneous and had an average thickness of about 0.2 mm.

EXAMPLE 10

A 100 ml solution for the non-adhesive backing layer was made using 84% by weight water USP, 0.02% by weight FD&C red 40 dye, 11% by weight hydroxyethyl cellulose (Mw $9 \times 10^4$), 1% by weight hydroxyethyl cellulose (Mw $7 \times 10^5$), 0.1% by weight of a 40% glyoxal aqueous solution, 3% by weight glyoxal, and 1% by weight menthol. Here, the glyoxal acted as a crosslinking agent, inducing a slow down in the erosion kinetics of the backing film. Also, the mixture of two different grades of hydroxyethyl cellulose was used to achieve slow release of the menthol. The film was coated on a polyester film as previously described.

EXAMPLE 11

A 100 ml solution for the adhesive layer was made using 88.6% by weight water USP, 1.8% by weight hydroxyethyl cellulose, Natrosol® 99-250 L NF (Aqualon), 2.6% by weight polyacrylic acid, Noveon® AA1 USP (BF Goodrich), 4.5% sodium carboxymethyl cellulose, cellulose gum 7 LF PH (Aqualon), and 2.5% by weight dyclonine HCl. Upon mixing, a suspension was formed.

Here, dyclonine HCl may be easily substituted with any other active pharmaceutical component. However, chemical characteristics of the active pharmaceutical, such as solubility, counter ions, and melting point, might require minor modifications of the overall process, such as dissolution in a particular solvent, changing the temperature of the solution, etc. The next example illustrates one slight modification.

EXAMPLE 12

A 100 ml solution for the adhesive layer was made using 74.6% by weight water USP, 1.8% by weight hydroxyethyl cellulose, 2.6% by weight polyacrylic acid, 4.5% sodium carboxymethyl cellulose, 2.5% by weight benzocaine, and 14% by weight ethyl alcohol. The use of benzocaine as the active pharmaceutical required that it first be dissolved in ethyl alcohol, given that benzocaine is more soluble in alcohol than water.

In the final solution, the benzocaine tends to precipitate in the form of a very fine powder. However, the film characteristics and bioadhesive properties remain intact.

EXAMPLE 13

A 100 ml solution for the adhesive layer was made using 91% by weight water USP, 2% by weight hydroxyethyl cellulose, 2.5% by weight polyacrylic acid, and 4.5% sodium carboxymethyl cellulose. The composition of the adhesive layer may be modified and may vary according the ranges described in Table 1 below:

TABLE 1

| Item # | % w | Material |
| --- | --- | --- |
| 1 | 60 to 99.5 | Water USP |
| 2 | 0.05 to 5 | Hydroxyethyl cellulose |
| 3 | 0.5 to 10 | Polyacrylic acid |
| 4 | 0.0 to 15 | Sodium Carboxymethyl cellulose |
| 5 | 0 to 10 | Polyvinyl pyrrolidone |

The relative part of each components depends of the chemical compatibility of the components and the residence time to be obtained.

EXAMPLE 14

A 100 ml solution for the adhesive layer was made using 90% by weight water USP, 1% by weight butacaine sulfate, 2% by weight hydroxyethyl cellulose, 2.5% by weight polyvinyl pyrrolidone, and 4.5% by weight sodium carboxymethyl cellulose. The solution was coated using a knife over roll on a Mylar substrate.

EXAMPLE 15

A 100 ml solution for the adhesive layer was made. The total composition of the solution was 48.6% water, 40% ethyl alcohol, 1.8% hydroxyethyl cellulose, 2.6% polyacrylic acid, 4.5% sodium carboxymethyl cellulose, and 2.5% dyclonine HCl. Here, however, the dyclonine HCl was first solubilized in 40 ml ethyl alcohol, and then, 48.6 ml of water were added to the dyclonine HCl/ethyl alcohol solution, followed by the addition of the other components.

The use of ethyl alcohol as an additional solvent resulted in a suspension which was slightly more viscous than that of Example 11, which used water as the only solvent.

EXAMPLE 16

Following the procedure of Example 12, a 100 ml solution for the adhesive layer was prepared. The solution was then coated following the procedure used in Example 1. The resulting film was 0.12 mm thick.

EXAMPLE 17

Following the procedure of Example 12, a 100 ml solution for the adhesive layer was prepared. The solution was coated on top of a backing film prepared according to Example 1. The opening of the knife was adjusted, taking into account the thickness of the backing film. After coating, the layered film was dried at 130° C. for 15 minutes. A 0.27 mm layered film of two layers was formed.

EXAMPLE 18

Following the procedure of Example 14, a bioadhesive film was prepared, except that the film was not fully dried. A backing film was prepared according to Example 1. The backing film was peeled off of its substrate and laminated on top of the bioadhesive film while still moist, and pressure was applied to seal the two films together. The pressure applied on the films resulted in a good interfacial adhesion. A 0.38 mm layered film of two layers was formed.

EXAMPLE 19

Following the procedure of Example 1, several solutions for backing films were prepared according to the compositions of Table 2 below. Following film formation, ½ inch disks were die cut and set on a double-sided tape. The tape was then positioned on a micro slide. The kinetics of erosion were evaluated in water: the slide was plunged into a 100 ml beaker of water stirred at a constant speed of 50 rpm. The time for erosion was measured from the moment the disk was fully immersed in the beaker of water. Percentages (%) refer to the concentration in solution.

TABLE 2

| Composition | Weight (mg)/Thickness (mm) | Erosion Time (min.) |
|---|---|---|
| 12% HEC (Mw $9 \times 10^4$) | 17.1/0.14 | 21 |
| 10% HEC (Mw $9 \times 10^4$) and 2% HEC (Mw $7 \times 10^5$) | 16.9/0.13 | 37 |
| 9% HEC (Mw $9 \times 10^4$) and 3% HEC (Mw $7 \times 10^5$) | 17/0.14 | 75 |
| 11.75% HEC ((Mw $9 \times 10^4$) and 0.25% HEC (Mw $1.3 \times 10^6$) | 17.1/0.14 | 69 |
| 11.95% HEC ((Mw $9 \times 10^4$) and 0.05% glyoxal (40% aq. sol.) | 17.2/0.13 | 57 |
| 11.99% HEC ((Mw $9 \times 10^4$) and 0.01% propylene glycol | 17.3/0.14 | 65 |

The results demonstrate that the erosion time varies, depending on the components of the formulation, assuming a similar surface state for each sample. Although water does not mimic the exact composition of saliva, and this experiment cannot precisely replicate in vivo residence times, the experiment provides an in vitro comparison of erosion times of various compositions for use in practicing the present invention.

EXAMPLE 20

½ inch diameter disks having a thickness of between 0.19 and 0.21 mm were administered to six healthy volunteers. The backing layer was prepared according to Example 1, and the adhesive layer was prepared according to Example 15, some containing dyclonine HCl as the active pharmaceutical component, and others containing benzocaine as a substitute. The adhesive layer was coated on top of the backing layer, forming a layered disk. The layered disk was set in the mouth, and the time for erosion was measured from the moment the disk was set in place.

Participants were asked to evaluate the disk's handling and numbing effect on a scale of 0 to 3, with 3 being very good, 2 good, 1 fair, and 0 poor. Participants also evaluated the time necessary for adhesion; the residence time; the foreign body sensation, if any, and its duration; and the erosion of the disk. Finally, participants were asked to evaluate the overall effectiveness of the disk and their overall impression, as well as which pharmaceutical component, dyclonine HCl (D) or benzocaine (B), they preferred. The results are described in Table 3 below.

TABLE 3

| No. | Handling | Adhesion | Residence Time | Foreign Body Sensation | Numbing | Dissolution | Efficiency | Overall | Pharmaceutical Pref. |
|---|---|---|---|---|---|---|---|---|---|
| 1 | 3 | instant | ~1 hr | <5 min. | 3 | did not notice | + | + | B |
| 2 | 2 | instant | ~1 hr | <5 min. | 3 | did not notice | + | + | B |
| 3 | 3 | instant | ~45 min. | no | 2 | did not notice | + | + | D |
| 4 | 3 | instant | ~45 min. | no | 2 | at the end | + | − | D |
| 5 | 2 | instant | ~30 min | <5 min. | 3 | at the end | + | + | D |
| 6 | 1 | difficult | ~15 min. | <5 min. | 2 | did not notice | − | − | D |

The results demonstrate that although the handling of the disk may be difficult for first time users, the adhesion is instantaneous, there is only a minor foreign body sensation which disappears after a couple minutes upon swelling of the disk, and numbing is effective.

EXAMPLE 21

A 1 kg preparation of a backing layer was made using 43.49% by weight of water, 43.49.% by weight of ethyl alcohol, 0.02% of FD&C red dye 40, 12% by weight of hydroxyethyl cellulose (Mw 9×104) and 1% by weight of 40% glyoxal aqueous solution. Then another 1 kg batch of the backing solution described at the example 1 was prepared. Using a Werner Mathis Labcoater, the substrate (Mylar 1000D or other polyester films such as 3M ScotchPak 1022) was set. 90 ml of the backing layer solution prepared according to example 1 was set in front of a knife over roll with an opening of 0.7 mm. The solution was then casted on the substrate and film dried for 8-9 min. at 130° C. Following the drying step, a 0.09 mm thick reddish film was the result. Then, the backing solution first described in this example was casted directly on the top of the first layer with the knife over roll technique using an opening of 0.8 mm. The resulting bilayer backing film was 0.15 mm thick.

EXAMPLE 22

A preparation of a backing layer obtained as described in example 5 was cast using a knife over roll and dried for 8-9 min. at 130° C. Then a preparation of a backing layer using 43.49% by weight of water, 43.49.% by weight of ethyl alcohol, 0.02% of FD&C red dye 40, 12% by weight of hydroxyethyl cellulose (Mw 9×104) and 1% by weight of 40% glyoxal aqueous solution was coated directly on the top of the previous dry film (first layer was 0.05 mm thick) The resulting bilayer backing film was 0.12 mm thick.

EXAMPLE 23

When a crosslinking agent is incorporated in the formulation, thermal curing allows to further crosslink the material either before or after the bioadhesive(s) layer(s) have been casted. Thermal curing of the films is performed by exposing the films to a time-temperature cycle. For instance, the film obtained at the end of example 22 might be exposed to 150° C. for 5 minutes, 120° C. for 10 minutes or any temperature/time which would accommodate the stability requirements of the film's components.

EXAMPLE 24

A preparation of a backing layer obtained as described in example 5 was cast using a knife over roll and dried for 8-9 min. at 130° C. A preparation of a backing layer using 42.49% by weight of water, 42.49.% by weight of ethyl alcohol, 0.02% of FD&C red dye 40, 11% by weight of hydroxyethyl cellulose (Mw 9×104), 2% by weight of polyethylene glycol 6000 and 2% by weight of propylene glycol was coated directly on the top of the previous dry film (first layer was 0.06 mm thick) The resulting bilayer backing film was 0.12 mm thick.

EXAMPLE 25

A preparation of a backing layer using 42.49% by weight of water, 42.49.% by weight of ethyl alcohol, 0.02% of FD&C red dye 40, 10% by weight of hydroxyethyl cellulose (Mw 9×104), 4% by weight of hydropropylcellulose (Mw 5 105) was coated using a knife over roll technique. Then directly on the top of the previous dry film (first layer was 0.07 mm thick) a backing preparation made from 42.49% by weight of water, 42.49.% by weight of ethyl alcohol, 0.02% of FD&C red dye 40, 12% by weight of hydroxyethyl cellulose (Mw 9×104) and 3% by weight of oleic acid, was casted and dried. The resulting bilayer backing film was 0.15 mm thick.

EXAMPLE 26

A preparation for the adhesive layer was made using 45.6% by weight water USP, 45% by weight of ethyl alcohol, 2% by weight hydroxyethyl cellulose, Natrosol® 99-250 L NF (Aqualon), 2.9% by weight polyacrylic acid, Noveon® AA1 USP (BF Goodrich), and 4.5% by weight of sodium carboxymethyl cellulose, cellulose gum 7 LF PH (Aqualon). This preparation is a bioadhesive preparation but does not contain any pharmaceutical.

EXAMPLE 27

A 100 ml solution for the adhesive layer was made using 45.1% by weight of water USP, 45% by weight of ethyl alcohol, 1.8% by weight hydroxyethyl cellulose, Natrosol® 99-250 L NF (Aqualon), 2.6% by weight polyacrylic acid, Noveon® AA1 USP (BF Goodrich), 4.5% sodium carboxymethyl cellulose, cellulose gum 7 LF PH (Aqualon), and 1% by weight terbutaline sulfate.

EXAMPLE 28

The film obtained following the example 25 is used as substrate for the final multilayer film of this example. The bioadhesive preparation of example 26 is directly casted on the film of example 25 and dried. Then the preparation of example 27 is cast on the top with a knife over roll system. The final four layer film is 0.240 mm. The composition of this film limits the release of terbutaline in the oral cavity but not completely as the pharmaceutical can still diffuse through the sides. In order to avoid this side diffusion, we have to changed slightly the design has previously mentioned.

EXAMPLE 29

The film obtained following the example 25 is used as substrate for the final multilayer film of this example. The bioadhesive preparation of example 26 is directly casted on the film of example 25 and dried. A trilayer film is thus obtained, the last layer being bioadhesive but not containing any drug. Then the preparation of example 27 is coated using a mask and dried (the mask is a 0.500 mm polyester film in which ellipsoids have been die cut deposited on the trilayer laminate). This step can be repeated if necessary. The mask is then delaminated. The resulting film is tri/four layers film composed of a laminate backing layer and a laminate bioadhesive layer in which the final component includes the pharmaceutical and is of a smaller surface as shown in figure. With this system, diffusion by either the sides or the back side is limited and allows an unidirectional release of the drug into the mucosal tissues.

EXAMPLE 30

Following the previous example but with fluocinonide instead of pilocarpine HCl, the same type of film is constructed using a screen coating technique instead of using a mask. Others techniques such as deposition of, spraying the solution or die cutting off the last layer, slot coating, or gravure coating, are satisfactory.

EXAMPLE 31

A 200 gram (g) backing solution (or backing collodion) for coating the backing layer was made by using 84.865% by weight ethyl alcohol 190F, 0.01% by weight of FD&C Red dye 40, 13.75% by weight of hydroxypropyl cellulose, 1.25% by weight ethylcellulose and 0.125% by weight of diethyl phathalate. This solution was prepared at ambient temperature by adding the ethyl cellulose to the solution of ethyl alcohol, dye, and and diethyl phathalate. The hydroxypropyl cellulose was then added and the collodion stirred for two hours.

A two layered film was subsequently obtained using a labcoater/dryer. On a Rexam 8024 substrate, 50 mL of the solution above was set in front of a knife-over-roll-coating device. The wet film was then dried for 6 minutes at 60° C. A second layer was directly coated on the top and the wet film was dried for an additional 6 minutes at 60° C. The final film thickness was measured to be 130 microns.

EXAMPLE 32

A 200 g backing solution (or backing collodion) for coating the backing layer was prepared as in Example 31 except that 84.74% by weight ethyl alcohol 190F, 0.01% by weight FD&C Red dye 40, 12.5% by weight hydroxypropyl cellulose, 2.5% by weight of ethylcellulose, and 0.25% by weight diethyl phathalate was used.

A film was obtained as in Example 31 except that the film thickness was 135 microns.

EXAMPLE 33

A 120 micron thick film was made in a similar manner as in Example 32 except that a higher molecular weight grade of ethyl cellulose was employed.

EXAMPLE 34

A 200 g backing solution (or backing collodion) for coating the backing layer was prepared as in Example 31 except that 84.74% by weight ethyl alcohol 190F, 0.01% by weight FD&C Red dye 40, 10% by weight hydroxypropyl cellulose, 5% by weight of ethylcellulose, and 0.5% by weight diethyl phathalate was used.

A film was obtained as in Example 31 except that the film thickness was 115 microns.

EXAMPLE 35

A 200 g backing solution (or backing collodion) for coating the backing layer was prepared as in Example 31 except that 81.99% by weight ethyl alcohol 190F, 0.01% by weight FD&C Red dye 40 and 18% by weight hydroxypropyl cellulose was used.

A film was obtained as in Example 31 except that the film thickness was 170 microns.

EXAMPLE 36

The disintegration time in water for the films of Examples 31 to 35 was measured by placing the films in a bath of water at 37±2° C. As the results in Table 4 show, the disintegration time varies with the ratio of hydroxypropyl cellulose to ethylcellulose.

TABLE 4

|  | Example 31 | Example 32 | Example 33 | Example 34 | Example 35 |
| --- | --- | --- | --- | --- | --- |
| Thickness (microns) | 130 | 135 | 120 | 115 | 170 |
| Disintegration time (min) | 20-25 | 25-30 | 35-40 | >60 | 15-20 |

EXAMPLE 37

A gel for the backing layers was prepared which contained 79.74% water, 0.01% FD&C red dye 40, 0.05% sodium benzoate, 2.5% peppermint flavor, 13.5% hydroxyethyl cellulose, and 4.5% hydroxypropyl cellulose by weight. The gel was then made into a two layer flexible backing film of 0.17 mm in thickness by first coating a 0.8 mm thick layer of the formulation on a substrate and then drying it at 80° C. for 8 minutes. A second 0.8 mm thick layer was then coated directly on top of the first layer and dried at 80° C. for 8 minutes. A sample of the two layer film was found to disintegrate in water within 10 minutes. While not wishing to be bound to any theory, it was believed that the hydrophilic salt modified the disintegration time and the hydroxypropyl cellulose improved the tensile strength of the film.

A gel for the bioadhesive layers was prepared which contained 45.2% water USP, 45.3% ethyl alcohol, 1.6% hydroxyethyl cellulose, 0.6% hydroxypropyl cellulose, 2.8% polyacrylic acid Noveon© AA1 USP, 2.5% sodium carboxymethyl cellulose, 0.1% titanium dioxide, and 1.9% albuterol sulfate by weight. Using the gel, a first bioadhesive layer of 0.5 mm was coated directly on top of the two layer flexible backing film and dried at 60° C. for 8 minutes. A second bioadhesive layer of 0.7 mm was then coated directly on top of the first bioadhesive layer and dried at 60° C. for 20 minutes. The final film was 0.330 mm in thickness, contained 5.92% water by weight, disintegrated in water in 15±3 minutes, and contained 1.46 mg/cm$^2$ albuterol sulfate. The final film also exhibited excellent tensile strength.

EXAMPLE 38

A gel for the backing layers was prepared which contained 42.49% water, 42.49.% ethyl alcohol, 0.02% of FD&C red dye 40, 14% hydroxyethyl cellulose (Mw 9×10$^4$), and 1% sweet peppermint by weight. Using the gel, a first backing layer of 0.7 mm was coated onto a substrate using a knife over roll technique. The layer was dried at 60° C. for 8 minutes. A second backing layer of 0.8 mm was then coated directly on top of the first backing layer and dried at 60° C. for 8 minutes. The final two layer film backing was 0.20 mm in thickness.

A gel for the bioadhesive layers was prepared which contained 45.95% water USP, 45.95% ethyl alcohol, 1.6% hydroxyethyl cellulose Natrosol® 99-250 L NF (Aqualon), 2.2% polyacrylic acid Noveon® AA1 USP (BF Goodrich), 3.4% sodium carboxymethyl cellulose cellulose gum 7 LF PH (Aqualon), and 0.9% albuterol sulfate by weight. Using the gel, a first bioadhesive layer of 0.5 mm was coated onto the two backing layers and dried at 60° C. for 10 minutes. A second bioadhesive layer of 0.8 mm was coated onto the first bioadhesive layer and dried at 60° C. for 20 minutes. The final film was 0.260 mm thick, disintegrated in water in 20±5 minutes, contained 5.6% water by weight and about 0.71 mg/cm$^2$ of albuterol sulfate.

EXAMPLE 39

A gel for the backing layers was prepared which contained 42.49% water, 42.49.% ethyl alcohol, 0.02% of FD&C red dye 40, 14% hydroxyethyl cellulose (Mw 9×10$^4$), and 1% sweet peppermint by weight. Using the gel, a first backing layer of 0.7 mm was coated onto a substrate using a knife over roll technique. The layer was dried at 60° C. for 8 minutes. A second backing layer of 0.8 mm was then coated directly on top of the first backing layer and dried at 60° C. for 8 minutes. The final two layer film backing was 0.20 mm in thickness.

A suspension for the bioadhesive layers was prepared which contained 45.95% water USP, 45.95% ethyl alcohol, 1.6% hydroxyethyl cellulose Natrosol® 99-250 L NF (Aqualon), 2.2% polyacrylic acid Noveon® AA1 USP (BF Goodrich), 3.4% sodium carboxymethyl cellulose cellulose gum 7 LF PH (Aqualon), and 0.9% testosterone by weight. The testosterone is insoluble in the formulation and is added as a micronized powder which stays in suspension. The viscosity of the formulation was lowered to facilitate the coating step by adding 10% by weight of alcohol:water in a 1:1 ratio. Using the suspension, a first bioadhesive layer of 0.5 mm was coated onto the two backing layers and dried at 60° C. for 10 minutes. A second bioadhesive layer of 0.9 mm was coated onto the first bioadhesive layer and dried at 60° C. for 20 minutes. The final film was 0.310 mm thick, disintegrated in water in 20±5 minutes, contained 5.3% of water by weight and about 0.64 mg/cm$^2$ of testosterone.

EXAMPLE 40

The films obtained via Examples 38 and 39 are die-cut in ½ inch diameter discs to be characterized and to be used for a systemic availability study in three dogs (20-25 kg spayed female bred hounds). One disc of the film to be evaluated is applied to the inside of the mouth on the buccal mucosa. A slight pressure is applied for 10 seconds. Then, the oral cavity is examined to assure adherence of the film to the mucosa and over the course of the study, to monitor the erosion of the discs. Using an indwelling jugular catheter, blood samples are collected at specific intervals. The serum is characterized by an ELISA assay in the case of albuterol sulfate and by an RIA method for the testosterone study. Mucosal tissues at the end of the studies did not show any sign of irritation.

After application of ½ inch diameter discs, systemic plasma levels obtained at different intervals are given in nanograms per milliliter for the mean of the three dogs. Drug loadings are 0.9 mg albuterol sulfate per disc and 0.8 mg testosterone per disc. Results are shown in Table 5 for the albuterol sulfate and in Table 6 for the testosterone.

TABLE 5

(albuterol sulfate)

| Time (minutes) | Mean (ng/ml) | Standard deviation |
|---|---|---|
| 0 | 0.12 | 0.01 |
| 5 | 0.15 | 0.12 |
| 10 | 0.22 | 0.07 |
| 15 | 0.57 | 0.54 |
| 30 | 1.51 | 1.61 |
| 60 | 6.01 | 4.75 |
| 90 | 8.90 | 3.99 |
| 120 | 11.66 | 2.97 |
| 150 | 11.22 | 3.49 |
| 180 | 9.90 | 1.21 |
| 240 | 6.30 | 2.21 |
| 360 | 6.29 | 2.23 |
| 480 | 3.75 | 0.62 |
| 720 | 1.00 | 1.05 |

TABLE 6

(testosterone)

| Time (minutes) | Mean (ng/ml) | Standard deviation |
|---|---|---|
| 0 | 0.00 | 0 |
| 5 | 2.21 | 1.48 |
| 10 | 4.68 | 2.55 |
| 15 | 3.81 | 2.06 |
| 30 | 2.87 | 2.32 |
| 60 | 3.73 | 3.31 |
| 90 | 4.82 | 3.53 |
| 120 | 7.14 | 0.51 |
| 150 | 3.20 | 0.03 |
| 180 | 0.62 | 0.18 |
| 240 | 0.18 | 0.20 |
| 360 | 0.12 | 0.18 |
| 480 | 0.02 | 0.04 |
| 720 | 0.01 | 0.01 |

These results illustrate that systemic delivery can be achieved with the pharmaceutical carrier devices of the invention. Moreover, the pharmaceutical carrier devices of the invention yield fast onset of activity, excellent bioavailability, and sustained delivery.

The invention claimed is:

1. A method for the transmucosal delivery of a systemic pharmaceutical for achieving a fast onset of activity in a subject or a desired level of a systemic pharmaceutical in the blood of a subject, comprising:
   adhering a bioerodable device to an oral mucosa surface of a subject such that there is minimal foreign body sensation; and
   directionally delivering an amount of a systemic pharmaceutical from the bioerodable device to mucosal tissue of the subject such that an effective amount of the systemic pharmaceutical is delivered to the subject achieving a fast onset of activity in the subject or a desired level of the systemic pharmaceutical in the blood of the subject within about 30 minutes,
wherein the bioerodable device has a residence time of less than 1 hour or about 1 hour, and the device comprises a thin and flexible adherent and bioerodable polymeric film containing a systemic pharmaceutical, and wherein the bioerodable device comprises soluble polymers selected based on dissolution rates to achieve the desired residence time and release profile.

2. The method of claim 1, comprising adhering the bioerodable device to a buccal mucosa surface.

3. The method of claim 1, wherein the device has a residence time of less than 30 minutes or about 30 minutes.

4. The method of claim 1, wherein the device has a thickness from about 0.1 mm and about 0.5 mm.

5. The method of claim 1, wherein the device has a surface area of from about 0.5 to about 20 square centimeters.

6. The method of claim 1, wherein the device further comprises a second pharmaceutical incorporated into the device.

7. The method of claim 1, wherein the device instantaneously adheres to the mucosal surface upon application.

* * * * *

UNITED STATES PATENT AND TRADEMARK OFFICE
CERTIFICATE OF CORRECTION

PATENT NO. : 7,579,019 B2  Page 1 of 1
APPLICATION NO. : 11/069089
DATED : August 25, 2009
INVENTOR(S) : Gilles H. Tapolsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,191 days.

In the Related U.S. Application Data section, please replace

"Continuation of application No. 09/684,682, filed on Oct. 4, 2000, now abandoned, which is a division of application No. 09/069,703, filed on Apr. 29, 1998, now abandoned, which is a continuation-in-part of application no. PCT/US97/18605, filed on Oct. 16, 1997"

with

"Continuation of application No. 09/684,682, filed on Oct. 4, 2000, now abandoned, which is a division of application No. 09/069,703, filed on Apr. 29, 1998, now abandoned, which is a continuation-in-part of application no. PCT/US97/18605, filed on Oct. 16, 1997 which is a PCT application claiming priority from 08/734,519, filed on Oct. 18, 1996, now patented as 5,800,832."

Signed and Sealed this
Twenty-fourth Day of May, 2011

David J. Kappos
*Director of the United States Patent and Trademark Office*